United States Patent
Kober et al.

(10) Patent No.: US 6,692,144 B1
(45) Date of Patent: Feb. 17, 2004

(54) METHOD FOR DETERMINING THE FREEZING TEMPERATURE OF A LIQUID, AND A DEVICE INTENDED THEREFORE

(75) Inventors: Rainer Kober, Darmstadt (DE); Sven Petzold, Wiesbaden (DE)

(73) Assignee: Mannesmann VDO AG, Frankfurt am Main (DE)

(*) Notice: Subject to any disclaimer, the term of this patent is extended or adjusted under 35 U.S.C. 154(b) by 0 days.

(21) Appl. No.: 09/565,595

(22) Filed: May 4, 2000

(30) Foreign Application Priority Data

May 4, 1999 (DE) .......................... 199 20 370

(51) Int. Cl.[7] .............................. G01N 25/04
(52) U.S. Cl. .............................. 374/16; 374/25
(58) Field of Search ................ 374/16, 25, 17, 374/18, 19, 20, 21; 73/863.11, 864.91

(56) References Cited

U.S. PATENT DOCUMENTS

| | | | | |
|---|---|---|---|---|
| 3,263,487 A | * | 8/1966 | Fiske, Jr. ............... | 374/16 |
| 3,436,956 A | * | 4/1969 | Fleming ............... | 374/25 |
| 3,667,280 A | * | 6/1972 | Simpson ............... | 374/25 |
| 3,695,093 A | * | 10/1972 | Hummel et al. ........ | 374/25 |
| 4,601,587 A | * | 7/1986 | Mathiprakasam ....... | 374/16 |
| 4,657,409 A | * | 4/1987 | Wiggin et al. ......... | 374/16 |
| 4,804,274 A | * | 2/1989 | Green .................. | 374/16 |
| 4,991,449 A | * | 2/1991 | Dieguez ............... | 73/863.11 |
| 5,141,329 A | * | 8/1992 | Orlando et al. ........ | 374/16 |
| 5,143,451 A | * | 9/1992 | Millgard ............... | 374/16 |
| 5,282,682 A | | 2/1994 | Orlando et al. | |
| 5,769,539 A | * | 6/1998 | Tsang et al. .......... | 374/16 |
| 5,833,366 A | * | 11/1998 | Ma .................... | 374/25 |
| 5,971,609 A | * | 10/1999 | Kijima et al. ......... | 374/17 |

FOREIGN PATENT DOCUMENTS

| | | |
|---|---|---|
| EP | 0045106 | 2/1982 |
| EP | 0225572 | 6/1987 |
| JP | 11051531 A | * 2/1999 |

OTHER PUBLICATIONS

EPO search report, Jul. 12, 2000.

* cited by examiner

Primary Examiner—Diego Gutierrez
Assistant Examiner—Madeline Gonzalez
(74) Attorney, Agent, or Firm—Mayer Brown Rowe & Maw LLP

(57) ABSTRACT

A method and measuring device intended for a window-cleaning system of a motor vehicle, wherein the freezing temperature is determined by continuous cooling of a representative partial volume of the liquid inside a chamber. For this purpose, measurements are made of the temperature while the liquid is cooled, which first drops in accordance with the heat dissipation until the start of the phase change initiating the freezing, and in the process leads the heat of solidification released to a temporary temperature plateau. The freezing temperature can be reliably determined in this way for each chemical composition of the liquid.

15 Claims, 1 Drawing Sheet

METHOD FOR DETERMINING THE FREEZING TEMPERATURE OF A LIQUID, AND A DEVICE INTENDED THEREFORE

FIELD OF THE INVENTION

The invention relates generally to an apparatus and a method for determining the freezing temperature of a liquid, and in particular the freezing temperature of a liquid in a liquid container of a motor vehicle.

BACKGROUND OF THE INVENTION

Methods and measuring devices for use in the early detection of the required antifreeze agent concentration in a liquid dropping below a prescribed desired value in a window-cleaning system in modem motor vehicles, and thus in avoiding possible damage by frost are known in principle. Such methods and measuring devices are operated, for example, with the aid of a visual and/or audible warning display.

However, such methods and measuring devices have disadvantages in that the cleaning liquid and antifreeze agents are essentially metered as judged by eye, since it is most often the case that neither the liquid container of the window-cleaning system, nor the antifreeze agent container have a suitable scale. Consequently, the metering instructions are therefore frequently not followed. It also turns out to be disadvantageous in that over time the liquid has added to it a multiplicity of different additives, such as polyhydric alcohols or surfactants whose composition and interaction can not easily be determined.

In order, nevertheless, to save the vehicle owner with troublesome manual checking, it is also conceivable to equip a measuring device with a chemical sensor which can detect the composition of the liquid and thus permit a conclusion to be drawn concerning the lowering of the freezing point by means of a control unit. In practice, however, it has emerged that deposits form on the surface of such a sensor and influence the measurement result. A constant high measuring accuracy therefore requires the sensor to be cleaned at regular intervals. The advantage obtained over a manual measurement is thereby completely lost.

Therefore, there is a need for a method and device which reliably give information about the freezing point of the liquid, even when used over a lengthy period. Other needs will become apparent upon a further reading of the following description taken in conjunction with the drawings.

SUMMARY OF THE INVENTION

The above mentioned needs are addressed, according to the present invention by a device and a method for determining the freezing temperature of a liquid in a motor vehicle. The present invention cools a partial volume of the liquid and, in the process, the temperature and the change in aggregate state of the liquid in the partial volume are detected. It is thereby possible to determine the freezing temperature of the liquid without knowing the exact composition of the liquid. At the same time, the method can deliver measurement results which remain reliable over a long period since, by comparison with chemical sensors, the temperature sensor is relatively insensitive and, in particular, requires no regular cleaning or maintenance. Substantially more accurate measurement results can be achieved in this case, since the freezing temperature is measured directly, and therefore the conclusion is drawn from the composition of the liquid as to the freezing temperature, and thus also, at the same time, a possible source of error is eliminated.

One embodiment of the new process is that the freezing point of the liquid can be determined by detecting a physical change in the aggregate state, for example, by using a pressure measuring cell which can detect the expansion associated with freezing. A particularly advantageous embodiment of the invention is, by contrast, achieved by virtue of the fact that the heat of solidification released upon the change in the aggregate state of the liquid located in the partial volume is detected as a delayed temperature decrease. In order to determine the freezing temperature, in this case the liquid partial volume is uniformly cooled in a chamber connected to the main liquid chamber. As the change from the liquid to the solid phase begins, the heat of the change is released as the heat of solidification. This heat of solidification can be detected by a cooling element as a delayed decrease in temperature—recorded, for example, by a temperature sensor—in conjunction with unchanged thermal dissipation. The freezing temperature is therefore determined with high accuracy from this temperature plateau, thus dispensing with the complete freezing of the liquid. By comparing the freezing temperature difference between the liquid and pure water, it is also possible to simultaneously deduce the concentration of additives lowering the freezing point.

Another advantage of the invention is that the invention detects changes in the electric admittance associated with the changes in the aggregate state of the liquid. The electric admittance or the electric resistance of the liquid is measured for this purpose. A central processing unit can be used to calculate a freezing temperature from a known temperature dependence of the admittance of the liquid. It is also conceivable to determine the freezing temperature by extrapolating representative values far above the freezing temperature.

Another advantage of the invention is that deviations in the calculation of the freezing temperature can be minimized by heating cooled liquid after determining the freezing temperature, and repeating the measuring process. Simultaneously, by heating the liquid beyond the level of the ambient temperature, the substances contained in the liquid are effectively mixed, thereby decreasing inaccuracies due to local differences in concentration.

It is also particularly useful to add an antifreeze agent, if appropriate, after the determination of the freezing temperature. By adding the antifreeze agent which lowers the freezing temperature, the freezing temperature can be set to a desired value without manual intervention. The antifreeze agent may be put into an auxiliary container connected to the liquid container, and can be fed to the liquid by means of an automatic valve. It is also conceivable to use the volumetric expansion upon freezing of the liquid for the purpose of delivering the antifreeze agent by, for example, using the volumetric expansion like a diaphragm pump to deliver the antifreeze agent.

Another advantage of the invention is that a signal for the motor vehicle occupant indicating that addition of antifreeze agent is required is triggered when the measured freezing temperature deviates from a desired value. The motor vehicle occupant is thereby informed about all relevant data, in order thus to be able to monitor the execution and the result of the determination of the freezing temperature, and take appropriate steps. In this case, it is also possible to determine the relationship between the determined freezing temperature of the liquid and the ambient temperature and, if appropriate, to trigger appropriate corresponding advice for the vehicle occupant.

The device, according to the present invention, determines the freezing temperature of a liquid, comprises of a chamber, enclosing a partial volume of the liquid, an opening in the chamber to permit an exchange of the liquid, a cooling element projecting into said chamber, and a sensor to determine the change in the aggregate state of the partial volume of liquid enclosed by the chamber and cooled by means of the cooling element.

It is thereby possible to reliably determine the freezing temperature of the liquid independently of the chemical composition. The liquid in the chamber is cooled in this case continuously by means of the cooling element until the measured temperature drops no further with continuing heat dissipation because of the heat of solidification being released. This temperature plateau simultaneously indicates the reaching of the freezing temperature, which can be detected by using the control unit to balance the dissipated heat with the measured temperature. Because only a partial volume of the liquid is cooled, while the remaining liquid volume is capable of further use, the small volume reduces the time and energy required to measure the freezing temperature.

Another particularly favorable configuration of the invention results when the device has a further sensor for detecting the aggregate state of the liquid. Such a sensor, designed as a pressure-measuring cell, for example, permits the freezing temperature to be determined accurately even if it is impossible to undertake reliable detection of the heat dissipated by the cooling element.

Also particularly simple is a development of the invention in which the further sensor is designed for determining the admittance of the liquid. As a result, the outlay associated with the freezing of the liquid can be reduced by calculating the freezing temperature in the case of a cooling of the liquid undertaken to a small extent, and of the change in the admittance measured in this case.

It is also particularly expedient in this case when the cooling element is a Peltier element. The thermal dissipation achieved by means of the Peltier element can be recalculated thereby without difficulty on the basis of the power consumption. At the same time, the Peltier element can also be used as a heating element in order in this way to be able to heat the liquid quickly after freezing, it also being possible at the same time to improve the mixing of the various constituents of the liquid.

It has proved to be particularly advantageous when the chamber enclosing a partial volume of liquid is arranged in the interior of the liquid container. Only a partial volume of the liquid is cooled, while the remaining liquid volume in the main container can be used further. The chamber may be arranged, for example, in the interior of the liquid container on a wall surface or bottom surface, and connected to the liquid container by means of a small opening. Furthermore, the device may be retroactively fitted without difficulty in the case of existing facilities and can be used to detect the temperature of a liquid in the liquid container even without being fixed. Another possibility of arranging the chamber is by connecting the chamber to the suction connection of the pump delivering the liquid.

It is particularly advantageous when liquid between the chamber and the liquid container may be exchanged by means of a valve. As a result, liquid is prevented from escaping, thus preventing warm liquid from flowing and allowing the temperature to be measured faster. Further, this configuration avoids measuring errors which can arise from partial freezing of individual constituents of the liquid.

The chamber may also be connected to the liquid container to simultaneously exchange the partial liquid volume inside the chamber each time the liquid container is filled with fresh liquid. Consequently, each filling of the liquid container with fresh liquid mixes the liquid inside the chamber. Thus, the contents of the partial liquid volume in the chamber substantially correspond to the liquid mixture in the liquid container such that local differences in concentration may be prevented. The chamber is fitted for this purpose in the region of the filling opening of the liquid container; thereby each time the liquid container is filled, the partial volume of liquid in the chamber is filled or emptied in accordance with the principle of a suction jet pump.

Another embodiment of the invention has the sensor of the device arranged inside an absorbent medium holding a partial volume of the liquid. The absorbent medium, designed as a sponge, for example, effectively prevents the cooled liquid from being exchanged with the remaining liquid outside the chamber. Consequently, only a small liquid volume needs to be cooled to determine freezing point. The absorbent medium can be used on the liquid container without structural changes. It is also possible to delimit a partial volume of the liquid by using a diaphragm.

The invention is suitable in principle for any liquids such as, for example, an engine coolant or a brake liquid. In the case of brake fluid, the invention may be applied in a similar way to determine the water content of the brake fluid. Additionally, the invention is particularly well-suited for measuring temperature of a cleaning liquid, in which the liquid is a liquid mixture with an antifreeze agent, because the invention allows the cleaning system to have any desired composition of the liquid mixture, and the device essentially does not require any kind of care or maintenance.

DETAILED DESCRIPTION OF THE PREFERRED EMBODIMENT

Figure 1:
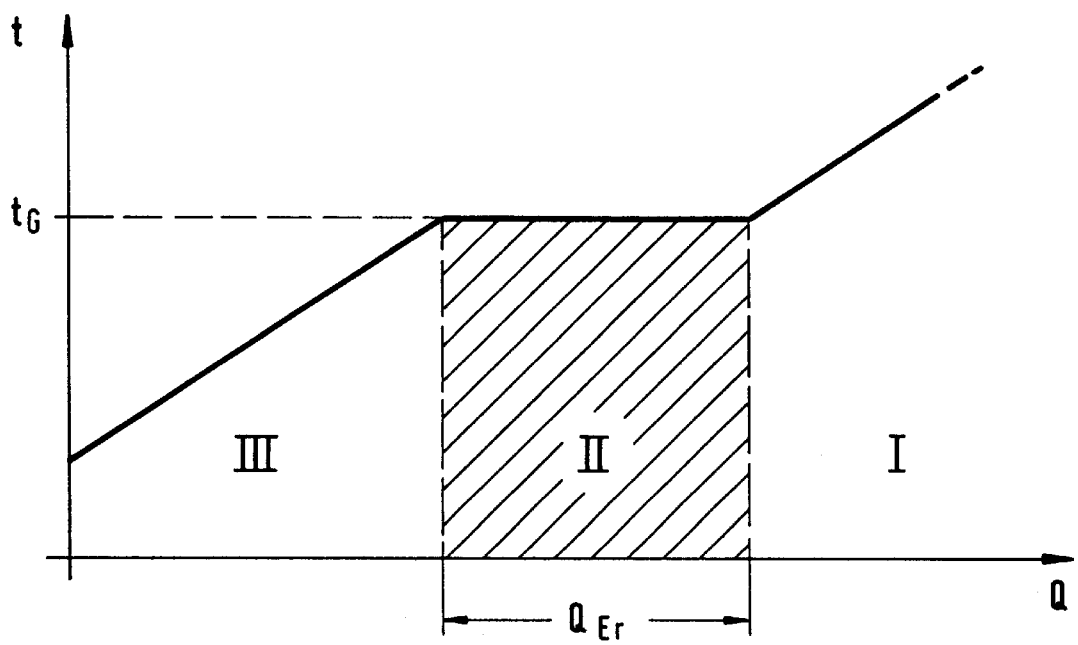
FIG. 1 shows a change of phase in a liquid under continuous cooling.

While the present invention is capable of embodiment in various forms, there is shown in the drawings and will be hereinafter described a number of presently preferred embodiments with the understanding that the present disclosure is to be considered as an exemplification of the invention, and is not intended to limit the invention to the specific embodiments illustrated in the drawings and described herein.

Figure 2:
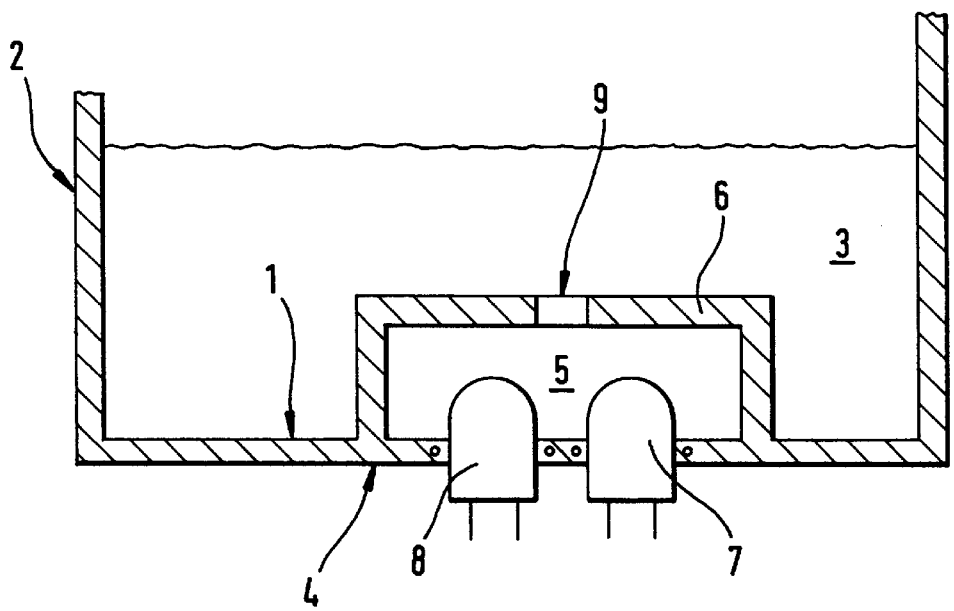
FIG. 2 shows a sectional side view of a liquid container having a device according to the invention for determining the freezing temperature of a liquid.

For purposes of illustration and not limitation, FIG. 1 shows a change of phase for a liquid under continuous cooling, and helps illustrate the principles of the device 4 described in more detail in FIG. 2 for determining the freezing temperature of a liquid in a motor vehicle. As heat $\Delta Q$ is continuously being dissipated in the liquid phase I, the measured temperature t of the liquid decreases linearly. When the liquid enters phase II, the measured temperature t remains essentially unchanged, however, because of the released heat of solidification $Q_{Er}$ in conjunction with continued dissipation of the heat $\Delta Q$. This plateau in the temperature is detected by comparing the measured temperatures t, and, therefore, characterizes the freezing temperature $t_G$ of the liquid. Only after phase II ends and the liquid enters into the solid phase III does the temperature t also drop further. The measuring principle of the measuring device 4 is therefore based on a comparative consideration of the measured temperature t as a function of the simultaneously dissipated heat $\Delta Q$ of the liquid. The dissipation of heat does not necessarily have to take place continuously. Furthermore, it is also not necessary to cool the liquid until phase II ends.

One embodiment of the present inventive device, for purposes of illustration not limitation, is shown in FIG. 2. FIG. 2 is a lateral sectional representation of a lower bottom region 1 of a liquid container 2, represented only partially, having a liquid 3. Arranged in the bottom region 1 of the liquid container 2 is a measuring device 4 with a chamber 6 enclosing a small partial volume 5 of the liquid 3. Projecting into this chamber 6 is a cooling element 7 which makes contact outside the liquid container 2 and is designed as a Peltier element, and a sensor 8 to determine the temperature. The cooling element 7 cools the partial volume of liquid 5 to determine the freezing temperature until a constant temperature of the liquid 3 is measured in conjunction with an unchanged heat dissipation. This temperature plateau simultaneously characterizes the change in phase illustrated in FIG. 1 and also marks the reaching of the freezing temperature. The chamber 6 is connected by means of an opening 9 to the liquid container 2, which is dimensioned such that the exchange of liquid proceeds substantially unhindered while a measuring operation can be performed in conjunction with a liquid 3 which is flowing only to an insignificant extent and has not cooled down.

The device 4 can also be equipped with a further sensor designed, for example, as a pressure-measuring cell to detect the phase change of the liquid. With such a sensor, the inventive device 4 can accurately determine the freezing temperature even when heat dissipated by the cooling element is unknown.

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. A method for determining the freezing temperature of an unknown liquid composition located in a liquid container comprising cooling a partial volume of the unknown liquid composition with a cooling element and detecting the temperature and the change in aggregate state of the unknown liquid composition in the partial volume with a sensor, wherein the partial volume is located within a partial volume container and wherein said partial volume container is located within the liquid container, said liquid container encompassing said partial volume container and wherein said cooling element is projecting into said partial volume container.

2. The method of claim 1, wherein said unknown liquid composition is a liquid mixture of a window cleaning system containing antifreeze.

3. The method of claim 1, wherein said unknown liquid composition is brake fluid.

4. The method of claim 1 further comprising detecting with the sensor the heat of solidification released in the partial volume upon the change in the aggregate state of the unknown liquid composition as a delayed temperature decrease.

5. The method of claim 1 further comprising heating the cooled unknown liquid composition after determining the freezing temperature, and repeating the measuring operation.

6. The method of claim 1, further comprising adding an antifreeze agent, if appropriate, allowing the determination of the freezing temperature.

7. The method of claim 1, further comprising triggering a signal for a motor vehicle occupant when the measured freezing temperature deviates from a desired value.

8. The method of claim 1, wherein the partial volume container permits an exchange of liquid between the partial volume container and the container though a single opening in the partial volume container.

9. A measuring device comprising a chamber, said chamber enclosing a partial volume of an unknown liquid composition and permitting an exchange of the unknown liquid composition between said chamber and a liquid container containing said unknown liquid composition, said chamber being located within the liquid container and said liquid container encompassing said chamber, a cooling element projecting into said chamber and a sensor for determining the change in the aggregate state of said partial volume of unknown liquid composition cooled by said cooling element.

10. The device of claim 9, wherein said cooling element is a Peltier element.

11. The device of claim 9, wherein said chamber is arranged in the interior of the liquid container.

12. The device of claim 9, wherein said chamber is connected to the liquid container in such a way that the exchange of the partial volume inside the chamber is simultaneously associated with feeding of fresh liquid.

13. The device of claim 9, wherein said unknown liquid composition is a liquid mixture of a window-cleaning system containing antifreeze.

14. The device of claim 9, wherein said unknown liquid composition is brake fluid.

15. The device of claim 9, wherein the chamber enclosing a partial volume permits the exchange of liquid between the chamber and the container through a single opening in the chamber.

* * * * *